(12) United States Patent
Tenney, III

(10) Patent No.: US 6,222,376 B1
(45) Date of Patent: Apr. 24, 2001

(54) CAPACITIVE MOISTURE DETECTOR AND METHOD OF MAKING THE SAME

(75) Inventor: Albert S. Tenney, III, North Wales, PA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/232,582

(22) Filed: Jan. 16, 1999

(51) Int. Cl.⁷ .......................... G01R 27/26; H01G 5/012
(52) U.S. Cl. ............................................ 324/664; 324/663
(58) Field of Search .................... 324/664, 663, 324/686, 689; 361/286

(56) References Cited

U.S. PATENT DOCUMENTS

| | | |
|---|---|---|
| 3,559,456 | 2/1971 | Lomker et al. . |
| 3,802,268 | 4/1974 | Thoma . |
| 4,429,343 | 1/1984 | Freud . |
| 4,482,882 | 11/1984 | Luder et al. . |
| 4,564,882 * | 1/1986 | Baxter et al. ........................ 361/286 |
| 4,831,493 * | 5/1989 | Wilson et al. ........................ 361/286 |
| 5,402,075 | 3/1995 | Lu . |
| 5,408,381 * | 4/1995 | Thoma et al. ........................ 361/286 |
| 5,596,266 * | 1/1997 | Mori et al. ............................ 324/446 |

* cited by examiner

Primary Examiner—Safet Metjahic
Assistant Examiner—James C Kerveros
(74) Attorney, Agent, or Firm—Joseph J. Kaliko

(57) ABSTRACT

An improved capacitive moisture detector includes a ceramic substrate with a plurality of layers of interdigitated electrodes and a plurality of interleaved moisture sensitive dielectric layers. Alternate electrodes are electrically coupled to provide two electrical contacts and a circuit representing multiple capacitors connected in parallel. According to an exemplary embodiment, six layers are provided resulting in a structure presenting five parallel connected capacitors thereby providing a total capacitance of the detector which is ten times that of a prior art detector having the same footprint. According to a preferred embodiment of the invention, each dielectric layer is made relatively thin to effectively decrease the distance between the plates of each of the five capacitors. Since capacitance is inversely proportional to the distance between the dielectric layers, the thinness of the electrodes in the present invention also serves to increase capacitance. It is estimated that the thinness of the dielectric layers can increase the total capacitance of the detector by a factor of three. According to another preferred embodiment of the invention, a floating porous conductive film is provided over the sixth electrode to contain the field of the top capacitor and render the detector immune from the effects of surface contaminants.

20 Claims, 4 Drawing Sheets

CAPACITIVE MOISTURE DETECTOR AND METHOD OF MAKING THE SAME

BACKGROUND OF THE INVENTION

1. Field of the Invention

The invention relates to an improved capacitance humidity sensing element for use in humidity measuring and control systems. More particularly, the invention relates to an improved capacitive moisture detector having greatly enhanced sensitivity and to a method of making such a detector.

2. Brief Description of the Related Art

Humidity can be measured by a number of techniques which are based upon the reversible water absorption characteristics of polymeric materials. The absorption of water causes a number of physical changes in the polymer. These physical changes can be transduced into electrical signals which are related to the water concentration in the polymer and which in turn are related to the relative humidity in the air surrounding the polymer.

Two of the most common physical changes are the change in resistivity and the change in dielectric constant which can be respectively translated into a resistance change and a capacitance change.

Arrangements utilizing the resistance change may, for example, be constructed in accordance with U.S. Pat. No. 3,559,456 to F. Lomker et al.

It has been found, however, that elements utilized as resistive components suffer from the disadvantage that there is an inherent dissipation effect caused by the dissipation of heat due to the current flow in the elements necessary to make a resistance measurement. The result is erroneous readings.

Elements constructed to approximate a pure capacitance avoid the disadvantages of the resistive elements. However, it is important in the construction of capacitive elements to avoid the problems which can arise with certain constructions for such elements.

Exemplary of the capacitive type element is the element shown in U.S. Pat. No. 3,802,268 to Paul E. Thoma.

In the '268 patent a sheet of cellulose acetate butyrate is sandwiched between two planar electrodes, one of which is porous to allow water molecules to equilibrate with the bulk of the film. Among the problems which are encountered with this type of construction is the slow response due to the thickness required to support the structure. There is also a difficulty in fabricating a conductive yet porous electrode.

In addition, there is also inaccuracy incurred at high relative humidity values in that the high water content causes problems due to excessive stress and the resulting mechanical shifts in the components of the element.

By making the component parts of the element thin, the above mentioned problems can be avoided and the capacitance type element can provide a fast, precise measurement of the relative humidity content of air over an extreme range of humidity as well as over an extreme range of temperature and pressure and other environmental variables.

Humidity sensing elements of the capacitance sensing type usually include a moisture insensitive, non-conducting structure with appropriate electrode elements mounted or deposited on the structure along with a layer or coating of dielectric, highly moisture sensitive material overlaying the electrodes and positioned so as to be capable of absorbing water from the surrounding atmosphere and reaching equilibrium in a short period of time.

A well regarded humidity sensing element of this type is disclosed in U.S. Pat. No. 4,429,343 issued to Freud and illustrated in prior art FIGS. 1–4.

Referring now to prior art FIG. 1, the humidity sensing element includes a planar non-conducting borosilicate glass substrate 10 with a thin metal film electrode system deposited thereon and a dielectric polymer coating 22.

The electrode system includes a first set of fingers 12 which are located in an interdigitated configuration with a second set of fingers 14. The fingers 12 are all connected in parallel to a common bus 16 which is in turn connected to the contact structure 18 at which point electrical contact is made with the measuring instruments to be used.

The other set of fingers 14 are connected in parallel to the bus 19 which is in turn connected to the contact 20, for which electrical connection is provided to the measuring instrument.

The interdigitated fingers are more clearly shown in the enlarged portion of the element shown in prior art FIG. 2 where it is shown that the distance from the center of a finger of one set to the center of the next finger of that set is identified as the period P.

The capacitance of this structure depends on the dielectric constant of the polymer coating. This dielectric constant changes depending on the amount of water vapor present in the coating. The amount of water vapor present in the coating depends on the water vapor partial pressure of the atmosphere ambient the coating and the water vapor partial pressure is proportional to relative humidity.

The structure of the element of prior art FIG. 1 and its relationship to the dielectric polymer coating 22 which overlays the fingers is shown in more detail in prior art FIG. 3 where the polymer 22 is shown overlaying fingers 12 and 14 which are shown as being deposited on the non-conducting substrate 10.

As shown in prior art FIG. 3, the thickness of the polymer coating is greater than the period of the fingers in order to minimize the effects of surface contamination. For example, if oil or grease contacts the surface of the coating, there will be a change in capacitance which is unrelated to relative humidity.

Since the capacitance between the sets of interdigitated fingers is determined by the weighted average of the dielectric constant of the polymer coating, that portion of the coating closest to the surface of the fingers must be weighted the most and that portion furthest from the fingers the least.

If the coating is thick enough there will be portions of the coating, at its surface and away from the fingers, which will be a sufficient distance from the surface of the fingers so as to have a negligible effect on the average dielectric constant. Thus, if the coating is maintained thick enough to place the surface far enough from the finger surface, the influence of contaminants on the surface should be negligible.

Devices of the type shown in prior art FIGS. 1–3 have been utilized to measure the relative humidity to an accuracy of 1% and a stability at 95% relative humidity of better than 1% in one month.

The solution presented in the '343 patent is based on the fact that the field used to make the capacitance measurement extends a certain distance normal to the electrodes. If the field extends beyond the surface of the polymer, contaminants on the surface of the polymer will affect the field. The problem with making the dielectric coating so thick that it captures all of the electric field is that the device becomes very slow in detecting changes in relative humidity.

Another approach to this problem is to make the electrodes and the period P smaller so that a relatively thin film dielectric could be used. This approach is limited by the resolution of the deposition technology used to place the electrodes on the substrate.

Another effective approach to the problem of surface contamination is illustrated in prior art FIG. 4.

According to this solution, a substrate 10' is printed with electrodes 12', 14' in the usual manner. A first thin film of dielectric polymer 22' is coated over the electrodes. A very thin porous conductor 23 is placed over the thin film 22' and a second thin polymer film 22" is coated over the conductor 23.

The theory behind this solution is that the conductor 23 captures most of the electric field and the second film 22" captures any of the field which manages to escape the conductor 23.

While this approach has merit, it does not render the detector any more sensitive than the other structures described above. In fact, the conductive layer 23 changes the circuit of the sensor to be two capacitors in series rather than a single capacitor. This reduces the capacitance by a factor of two and thus decreases the sensitivity of the detector.

Modern manufacturing processes require measurement of moisture contents corresponding to dew points below −40 degrees C or a relative humidity of less than 0.1%.

There is a need for a durable, compact, efficient moisture detector which can be used effectively in these processes to measure very small moisture content in gaseous atmospheres.

SUMMARY OF THE INVENTION

It is therefore an object of the invention to provide an improved capacitive moisture detector.

It is also an object of the invention to provide an improved capacitive moisture detector which is not adversely affected by surface contamination.

It is another object of the invention to provide an improved capacitive moisture detector which is more sensitive and capable of detecting very small quantities of moisture.

It is still another object of the invention to provide an improved capacitive moisture detector which is compact.

In accord with these objects which will be discussed in detail below, the improved capacitive moisture detector of the present invention includes a ceramic substrate with a first interdigitated electrode deposited thereon, a first moisture sensitive dielectric film covering the first electrode, a second interdigitated electrode deposited on the first film, a second moisture sensitive dielectric film covering the second electrode, a third interdigitated electrode deposited on the second film, a third moisture sensitive dielectric film covering the third electrode, a fourth interdigitated electrode deposited on the third film, a fourth moisture sensitive dielectric film covering the fourth electrode, a fifth interdigitated electrode deposited on the fourth film, a fifth moisture sensitive dielectric film covering the fifth electrode, a sixth interdigitated electrode deposited on the fifth film, and a sixth moisture sensitive dielectric film covering the sixth electrode.

The first, third, and fifth electrodes are electrically coupled to each other and form a first electrical contact for the detector. The second, fourth, and sixth electrodes are electrically coupled to each other and form a second electrical contact for the detector. The resulting structure presents five parallel connected capacitors thereby providing a total capacitance of the detector which is ten times that of a prior art capacitor having the same footprint.

According to a preferred embodiment of the invention, each dielectric layer is made relatively thin to effectively decrease the distance between the electrodes of each of the five capacitors. Since capacitance is inversely proportional to the distance between the electrodes, the thinness of the dielectric layers in the present invention also serves to increase capacitance.

It is estimated that the thinness of the dielectric layers can increase the total capacitance of the detector by a factor of three.

According to another preferred embodiment of the invention, a floating porous conductive film is provided over the sixth electrode to contain the field of the top capacitor and render the detector immune from the effects of surface contaminants.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
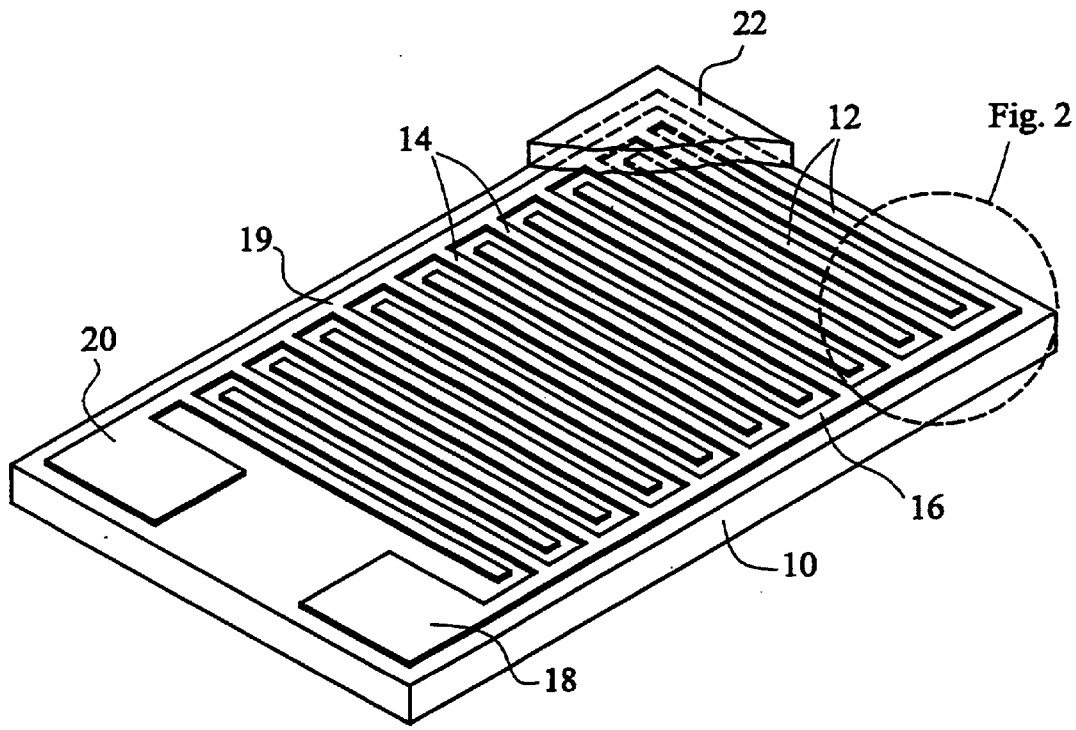
FIG. 1 is a partially cut away perspective view of a prior art moisture sensor.
Figure 2:
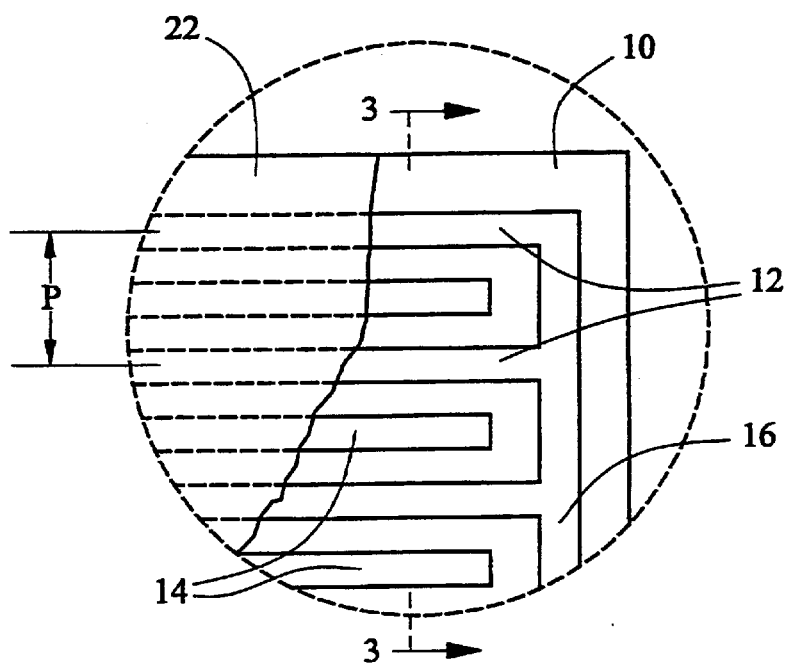
FIG. 2 is a broken partially cut away enlarged detail of the indicated portion in prior art FIG. 1.
Figure 3:
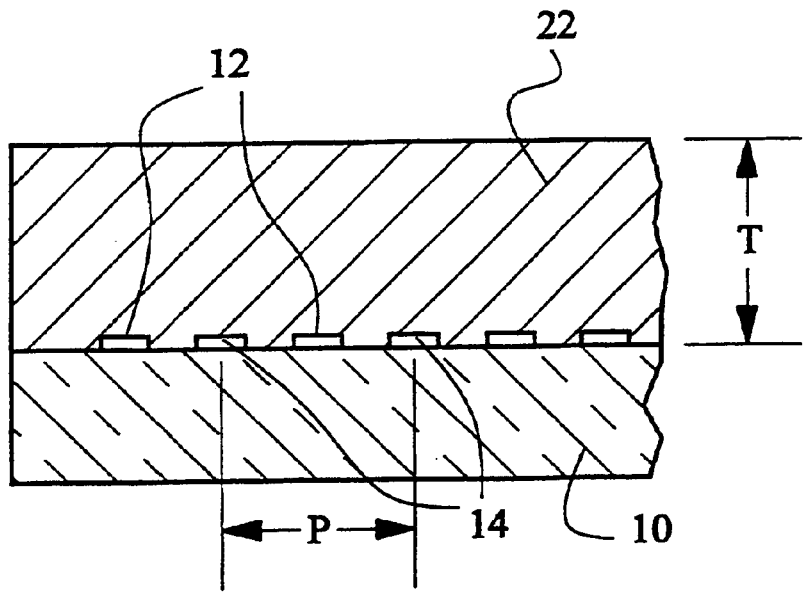
FIG. 3 is a section taken along line 3—3 in prior art FIG. 2.
Figure 4:
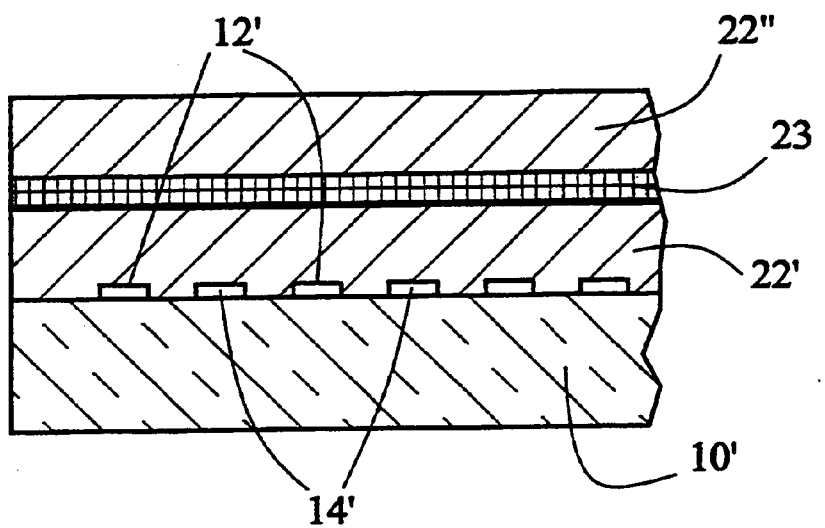
FIG. 4 is a view similar to FIG. 3 of another prior art moisture sensor.
Figure 5:
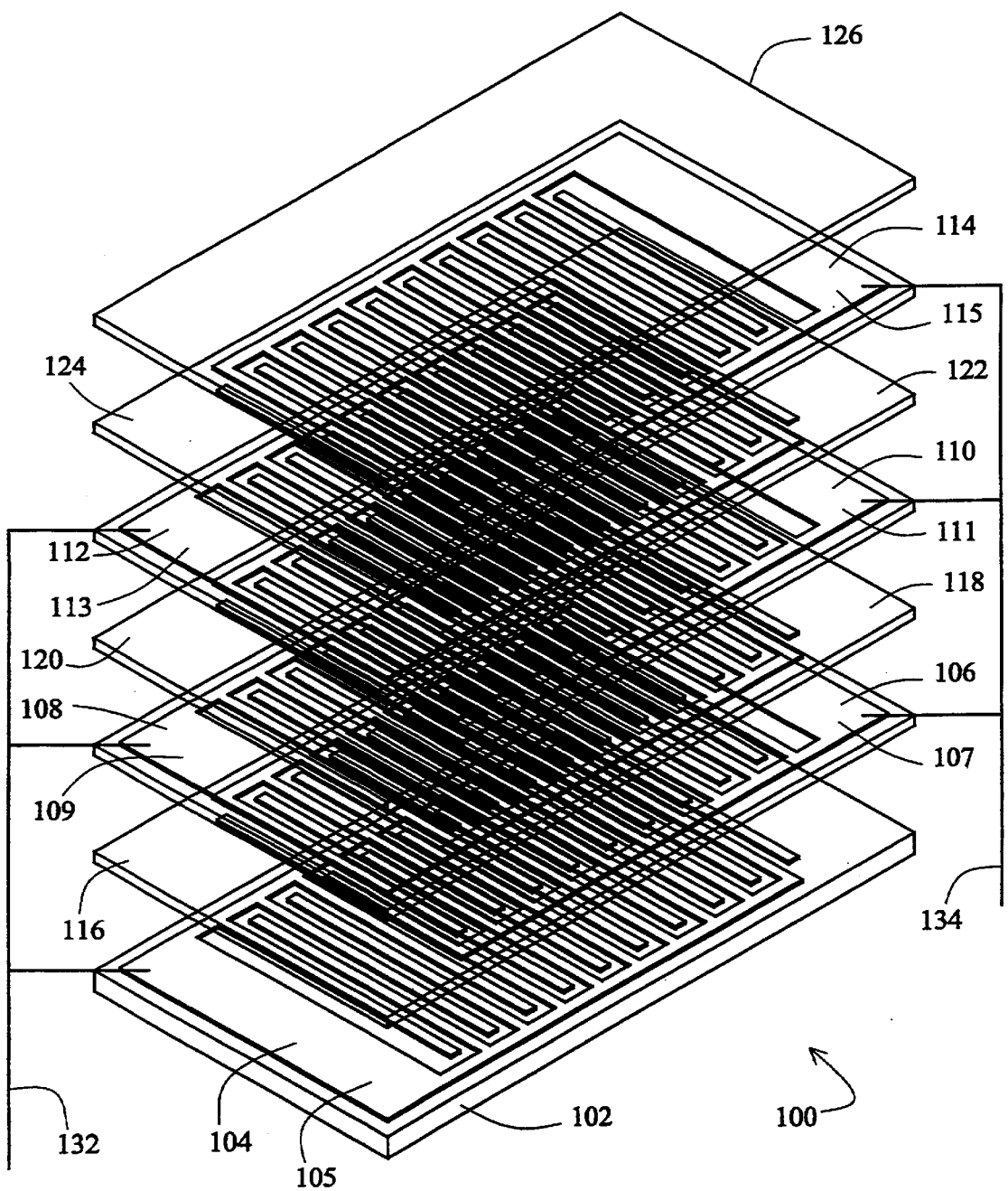
FIG. 5 is an exploded perspective view of one embodiment of the moisture detector according to the invention.
Figure 6:
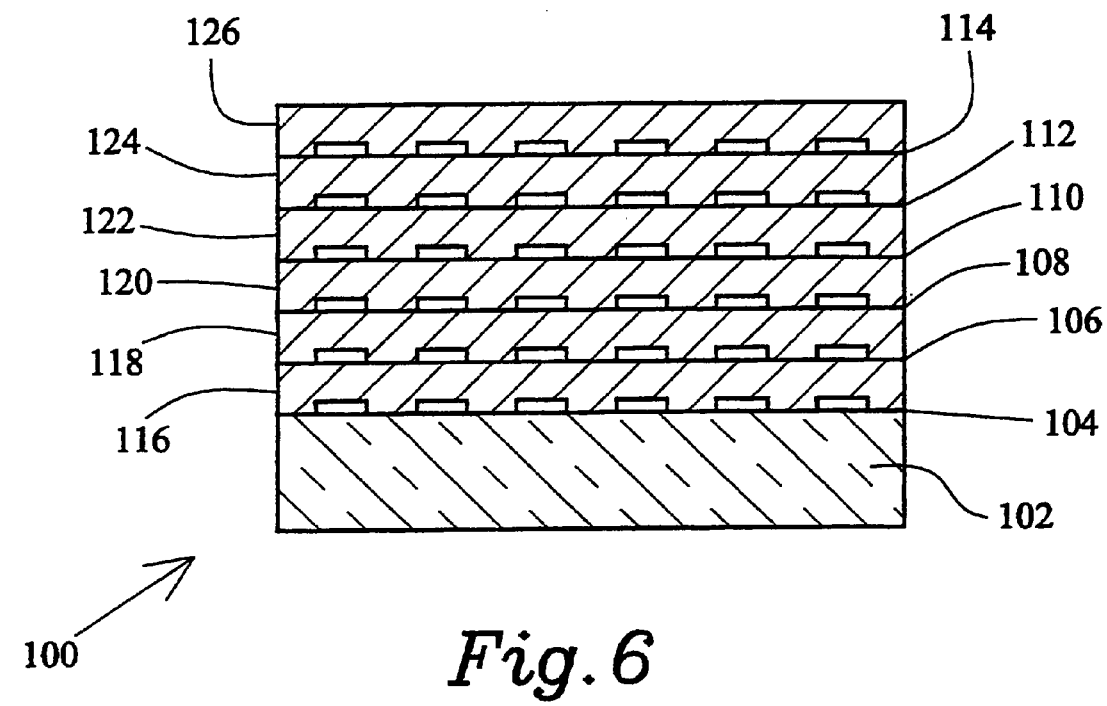
FIG. 6 is a sectional view of the moisture detector of FIG. 5 after assembly.

Referring now to FIGS. 5 and 6, the improved capacitive moisture detector 100 of the present invention includes a ceramic substrate 102 with a plurality of layers of interdigitated electrodes, for example 104, 106, 108, 110, 112, 114, and a plurality of interleaved moisture sensitive dielectric layers, for example 116, 118, 120, 122, 124, 126.

Alternate electrodes are electrically coupled to provide two electrical contacts, e.g. 132 and 134, and a circuit representing multiple, e.g. five, capacitors connected in parallel.

More particularly, according to the invention, a conventional ceramic substrate of conventional size, e.g. 4 mm by 6 mm is obtained and a first interdigitated electrode 104 deposited thereon.

The electrode 104 includes a plurality of inter digitated fingers similar to the prior art electrodes but with all of the fingers electrically coupled to a single contact pad 105.

A first moisture sensitive dielectric film 116 is obtained and placed on top of the first electrode 104 in a conventional manner. The thickness of the film 116 is preferably approximately 1,000–2,000 Angstroms.

According to the invention, a second interdigitated electrode 106 deposited on the first film 116. The deposition of the second electrode onto the first film may be accomplished before the film is layered onto the first electrode.

The second electrode 106 is substantially the same as the first electrode 104 but is in a reversed orientation with its electrical contact pad 107 being located at one end of the substrate 102 opposite to the end where the contact pad 105 is located.

According to the presently preferred embodiment of the invention, additional layers of moisture sensitive dielectric film with additional electrodes are layered one upon the other as shown in FIGS. 5 and 6.

Specifically, a second moisture sensitive dielectric film 118 covers the second electrode 106. A third interdigitated electrode 108 is deposited on the second film 118. A third moisture sensitive dielectric film 120 covers the third electrode 108 and a fourth interdigitated electrode 110 is deposited on the third film 120. A fourth moisture sensitive dielectric film 122 covers the fourth electrode 110 and a fifth interdigitated electrode 112 is deposited on the fourth film 122. A fifth moisture sensitive dielectric film 124 the fifth electrode 112 and a sixth interdigitated electrode 114 is deposited on the fifth film 124. A sixth moisture sensitive dielectric film 126 covers the sixth electrode 114.

The electrical contact pads 105, 109, and 113 of the first electrode 104, the third electrode 108, and the fifth electrode 112 are electrically coupled to each other and form a first electrical contact 132 for the detector 100.

The electrical contact pads 107, 111, and 115 of the second electrode 106, the fourth electrode 110, and the sixth electrode 114 are electrically coupled to each other and form a second electrical contact 134 for the detector 100.

Those skilled in the art will appreciate that the resulting structure presents five parallel connected capacitors thereby providing a total capacitance of the detector which is ten times that of a prior art capacitor having the same footprint. Further, since each electrode layer is made relatively thin, this effectively decreases the distance between the plates of each of the five capacitors.

Since capacitance is inversely proportional to the distance between the electrodes, the thinness of the dielectric layers in the present invention also serves to increase capacitance.

According to the specifications provided above, the moisture detector 100 has a total capacitance which is approximately thirty times that of a conventional detector having the same footprint.

Figure 7:
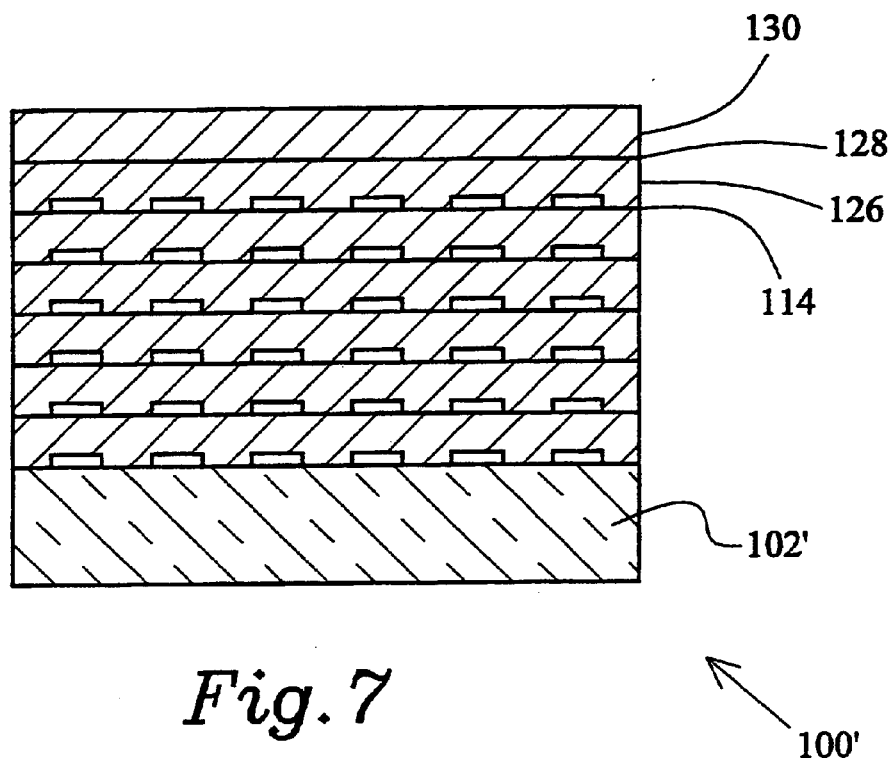
FIG. 7 is a view similar to FIG. 6 of a second embodiment of the invention.

Turning now to FIG. 7, a further preferred embodiment of the detector 100' is substantially the same as the detector 100 described above but includes a floating porous conductive film 128 above the sixth electrode 114 to contain the field of the top capacitor and render the detector immune from the effects of surface contaminants.

Preferably, the conductive film 128 is placed on top of the sixth moisture sensitive dielectric film 126 and is covered by a seventh moisture sensitive dielectric film 130.

There have been described and illustrated herein several embodiments of an improved capacitive moisture detector and methods of making it.

While particular embodiments of the invention have been described, it is not intended that the invention be limited thereto, as it is intended that the invention be as broad in scope as the art will allow and that the specification be read likewise.

Thus, while a particular number of electrode layers has been disclosed, it will be appreciated that more or fewer layers could be utilized with the minimum number of layers being three to provide two parallel connected capacitors.

Also, while particular geometries have been shown for the electrodes, it will be recognized that other types of geometries could be used with similar results obtained provided that the electrodes are moisture permeable.

Furthermore, while particular materials have been disclosed, it will be understood that different materials can achieve the same or similar function as disclosed herein.

It will therefore be appreciated by those skilled in the art that yet other modifications could be made to the provided invention without deviating from its spirit and scope as so claimed.

What is claimed is:

1. A capacitive moisture sensor, comprising:
   (a) a non-conductive substrate;
   (b) a first electrode deposited on said substrate;
   (c) a first moisture sensitive porous dielectric film covering and protecting said first electrode, including the edges thereof, from exposure to non-vaporous contaminants;
   (d) a second electrode deposited on said first moisture sensitive porous dielectric film;
   (e) a second moisture sensitive porous dielectric film covering and protecting said second electrode, including the edges thereof, from exposure to non-vaporous contaminants;
   (f) a third electrode deposited on said second moisture sensitive porous dielectric film, said third electrode being electrically coupled to said first electrode;
   (g) a first electrical contact for said sensor, said first electrical contact being electrically coupled to said first electrode and said third electrode; and
   (h) a second electrical contact electrically coupled to said second electrode.

2. A sensor according to claim 1 wherein each of said electrodes have a plurality of interdigitated fingers.

3. A sensor according to claim 1 wherein each of said electrodes is moisture permeable.

4. A sensor according to claim 1 wherein each of said moisture sensitive porous dielectric films is approximately 1,000 to 2,000 Angstroms thick.

5. A sensor according to claim 1 further comprising a third moisture sensitive porous dielectric film covering said third electrode.

6. A sensor according to claim 1 further comprising a porous conductive film located above said third electrode and electrically isolated from each of said electrodes.

7. A sensor according to claim 5 further comprising:
   (a) a fourth electrode deposited on said third moisture sensitive porous dielectric film, said fourth electrode being electrically coupled to said second electrode;
   (b) a fourth moisture sensitive Porous dielectric film covering said fourth electrode;
   (c) a fifth electrode deposited on said fourth moisture sensitive porous dielectric film, said fifth electrode being electrically coupled to said third electrode;
   (d) a fifth moisture sensitive porous dielectric film covering said fifth electrode; and
   (e) a sixth electrode deposited on said fifth moisture sensitive porous dielectric film, said sixth electrode being electrically coupled to said fourth electrode.

8. A sensor according to claim 7 further comprising a sixth moisture sensitive porous dielectric film covering said sixth electrode.

9. A sensor according to claim 8 further comprising a porous conductive film located above said sixth electrode and electrically isolated from each of said electrodes.

10. A sensor according to claim 9 further comprising a seventh moisture sensitive porous dielectric film covering said porous conductive film.

11. A method of making a capacitive moisture sensor, comprising the steps of:
(a) depositing a first electrode on a non-conductive substrate;
(b) covering and protecting the first electrode, including the edges thereof, with a first moisture sensitive porous dielectric film, thereby protecting said first electrode from exposure to non-vaporous contaminants;
(c) depositing a second electrode on the first moisture sensitive porous dielectric film;
(d) covering and protecting the second electrode, including the edges thereof, with a second moisture sensitive porous dielectric film, thereby protecting said second electrode from exposure to non-vaporous contaminants;
(e) depositing a third electrode on the second moisture sensitive porous dielectric film;
(f) electrically coupling the third electrode to the first electrode;
(g) electrically coupling a first electrical contact for said sensor to the first electrode and the third electrode; and
(h) electrically coupling a second electrical contact for the sensor to the second electrode.

12. A method according to claim 11 wherein said steps of depositing includes depositing the electrodes with interdigitated fingers.

13. A method according to claim 11 wherein said steps of depositing includes depositing the electrodes to be moisture permeable.

14. A method according to claim 11 wherein said steps of covering includes covering the electrodes with porous film approximately 1,000–2,000 Angstroms thick.

15. A method according to claim 11 further comprising the step of covering the third electrode with a third moisture sensitive porous dielectric film.

16. A method according to claim 11 further comprising the step of placing a porous conductive film above the third electrode and electrically isolating it from each of the electrodes.

17. A method according to claim 16 further comprising the steps of:
(a) depositing a fourth electrode on the third moisture sensitive porous dielectric film;
(b) electrically coupling the fourth electrode to the second electrode;
(c) covering the fourth electrode with a fourth moisture sensitive porous dielectric film;
(d) depositing a fifth electrode on the fourth moisture sensitive porous dielectric film;
(e) electrically coupling the fifth electrode to the third electrode;
(f) covering the fifth electrode with a fifth moisture sensitive porous dielectric film;
(g) depositing a sixth electrode on the fifth moisture sensitive porous dielectric film; and
(h) electrically coupling the sixth electrode to the fourth electrode.

18. A method according to claim 17 further comprising the step of covering the sixth electrode with a sixth moisture sensitive porous dielectric film.

19. A method according to claim 18 further comprising the step of placing a porous conductive film above the sixth electrode and electrically isolating it from each of the electrodes.

20. A method according to claim 19 further comprising the step of covering the porous conductive film with a seventh moisture sensitive porous dielectric film.

* * * * *